US00PP12983P2

(12) United States Plant Patent
Glicenstein

(10) Patent No.: US PP12,983 P2
(45) Date of Patent: Sep. 17, 2002

(54) CHRYSANTHEMUM PLANT NAMED 'YOANDREA'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 39 days.

(21) Appl. No.: 09/837,583

(22) Filed: Apr. 19, 2001

(51) Int. Cl.[7] ..... A01H 5/00
(52) U.S. Cl. ..... Plt./290
(58) Field of Search ..... Plt./287, 290

*Primary Examiner*—Howard J. Locker
(74) *Attorney, Agent, or Firm*—C. A. Whealy

(57) ABSTRACT

A distinct cultivar of Chrysanthemum plant named 'Yoandrea', characterized by its upright plant habit; freely branching growth habit; uniform and freely flowering habit; decorative-type inflorescences; and dark reddish bronze ray florets.

1 Drawing Sheet

BACKGROUND OF THE INVENTION

The present invention relates to a new and distinct cultivar of Chrysanthemum plant, botanically known as *Chrysanthemum×morifolium* and hereinafter referred to by the name 'Yoandrea'.

The new cultivar is a product of a planned breeding program conducted by the Inventor in Salinas, Calif. and Fort Myers, Fla. The objective of the breeding program is to create new garden-type Chrysanthemum cultivars having inflorescences with desirable inflorescence forms, attractive floret colors and good garden performance.

The new Chrysanthemum originated from a cross made by the Inventor in November, 1993, in Salinas, Calif., of the Chrysanthemum cultivar Peachy Lynn, disclosed in U.S. Plant Pat. No. 8,892, as the female, or seed, parent with an unnamed Chrysanthemum proprietary seedling selection, as the male, or pollen, parent. The new Chrysanthemum was discovered and selected by the Inventor as a single flowering plant within the progeny of the stated cross grown in a controlled environment in Fort Myers, Fla. in November, 1996. The selection of this plant was based on its desirable inflorescence form, attractive ray floret color and good garden performance.

Asexual reproduction of the new cultivar by terminal cuttings taken in a controlled environment in Fort Myers, Fla. since January, 1997, has shown that the unique features of this new Chrysanthemum are stable and reproduced true to type in successive generations.

SUMMARY OF THE INVENTION

The cultivar Yoandrea has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoandrea'. These characteristics in combination distinguish 'Yoandrea' as a new and distinct cultivar:

1. Upright plant habit.
2. Freely branching, dense, full plants.
3. Uniform and freely flowering.
4. Decorative-type inflorescences.
5. Dark reddish bronze-colored ray florets.

Plants of the new Chrysanthemum can be compared to plants of the female parent, the cultivar Peachy Lynn. In side-by-side comparisons conducted by the Inventor in Salinas, Calif., plants of the new Chrysanthemum differ from plants of the cultivar Peachy Lynn in the following characteristics:

1. Plants of the new Chrysanthemum are much larger than plants of the cultivar Peachy Lynn.
2. Plants of the new Chrysanthemum flower about two weeks later than plants of the cultivar Peachy Lynn.
3. Plants of the new Chrysanthemum are stronger and are less susceptible to breakage when compressed than plants of the cultivar Peachy Lynn.
4. Ray florets of plants of the new Chrysanthemum and the cultivar Peachy Lynn differ in color.

Compared to plants of the male parent, plants of the new Chrysanthemum differ in ray floret color.

Plants of the new Chrysanthemum can be compared to plants of the cultivar Glowing Lynn, disclosed in U.S. Plant Pat. No. 10,038. In side-by-side comparisons conducted by the Inventor in Salinas, Calif., plants of the new Chrysanthemum differ from plants of the cultivar Glowing Lynn in the following characteristics:

1. Plants of the new Chrysanthemum are larger than plants of the cultivar Glowing Lynn.
2. Plants of the new Chrysanthemum flower about two weeks later than plants of the cultivar Glowing Lynn.
3. Plants of the new Chrysanthemum are stronger and are less susceptible to breakage when compressed than plants of the cultivar Glowing Lynn.
4. Plants of the new Chrysanthemum have larger inflorescences than plants of the cultivar Glowing Lynn.
5. Ray florets of plants of the new Chrysanthemum and the cultivar Glowing Lynn differ in color.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Yoandrea'.

The photograph at the bottom of the sheet comprises a close-up view of typical inflorescences of the cultivar 'Yoandrea'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate those generally used in commercial garden Chrysanthemum production. One rooted cutting was planted in a 15-cm container in July, 2000 and plants were grown under natural season conditions. Plants were not pinched, that is, the terminal apex was not removed to enhance branching. Measurements and numerical values represent averages for typical flowering plants.

Botanical classification: *Chrysanthemum×morifolium* cultivar Yoandrea.

Commercial classification: Decorative-type garden Chrysanthemum.

Parentage:

*Female, or seed, parent.*—*Chrysanthemum× morifolium* cultivar Peachy Lynn, disclosed in U.S. Plant Pat. No. 8,892.

*Male, or pollen, parent.*—Unnamed *Chrysanthemum× morifolium* proprietary seedling selection, not patented.

Propagation:

*Type.*—Terminal tip cuttings.

*Time to initiate roots.*—About four days at 21° C.

*Time to produce a rooted cutting.*—About ten days at 21° C.

*Root description.*—White, fine and fibrous.

*Rooting habit.*—Freely branching.

Plant description:

*Appearance.*—Perennial herbaceous decorative-type garden Chrysanthemum. Inverted triangle; upright plant form. Stems initially upright, then somewhat outwardly spreading giving a uniformly mounded to flat-top appearance to the plant. Freely branching with about 8 lateral branches per plant. Strong sturdy plants that resist breakage when compressed.

*Plant height.*—About 24 cm.

*Plant diameter.*—About 28 cm.

*Lateral branches.*—Length: About 18 cm. Diameter: About 6 mm. Internode length: About 1.2 cm. Aspect: Mostly upright. Texture: Pubescent. Color: 146A overlain with anthocyanin, close to 187A.

*Foliage description.*—Leaf arrangement: Alternate. Length: About 4.4 cm. Width: About 3.4 cm. Apex: Cuspidate to mucronate. Base: Attenuate to truncate. Margin: Palmately lobed, sinuses mostly divergent. Texture: Both surfaces, pubescent; veins prominent on lower surface. Color: Young foliage upper surface: Darker than 147A. Young foliage lower surface: Slightly darker than 147B. Mature foliage upper surface: Slightly darker than 147A. Mature foliage lower surface: Slightly darker than 147B. Venation, upper surface: 147A. Venation, lower surface: 147B. Petiole length: About 1.4 cm. Petiole diameter: About 2 mm. Petiole color, both surfaces: Close to 146B.

Inflorescence description:

*Appearance.*—Decorative-type inflorescence form with elongated oblong-shaped ray florets. Inflorescences borne on terminals above foliage, arising from leaf axils. Disk and ray florets arranged acropetally on a capitulum. About 9 inflorescences per lateral; about 72 inflorescences per plant.

*Flowering response.*—Under natural season conditions, plants flower in late October in the Northern Hemisphere and continue to flower for at least three weeks depending on weather conditions.

*Inflorescence bud* (*before showing color*).—Height: About 5 mm. Diameter: About 7 mm. Phyllary color: 143A.

*Inflorescence size.*—Diameter: About 4.8 cm. Depth (height): About 2 cm. Disc diameter: About 2 mm or less, inconspicuous. Receptacle diameter: About 6 mm.

*Ray florets.*—Shape: Elongated oblong. Length: About 2.3 cm. Corolla tube length: About 4 mm. Width: About 5 mm. Apex: Acute, emarginate or dentate. Margin: Entire. Texture: Smooth, glabrous, satiny. Orientation: Initially upright and incurved, then perpendicular to the peduncle and concave to flat. Number of ray florets per inflorescence: About 278. Color: When opening, upper and lower surfaces: Close to 185A. Opened inflorescence, upper surface: 9A to 12A overlain with 45A or 46A, red more prominent at margins; with subsequent development, reddish overtones less prominent. Overall tonality, close to 163A to 163B. Opened inflorescence, lower surface: 9B to 9C underlain with close to 53A. Overall tonality, close to 163A with reddish overtones.

*Disc florets.*—Shape: Tubular, apex dentate. Length: About 6 mm. Width: Apex: About 1.5 mm. Base: About 1 mm. Number of disc florets per inflorescence: Less than 20. Color: Immature: 154A to 9A. Mature: Apex: 9A to 12A. Mid-section: 154D. Base: 155D.

*Peduncle.*—Aspect: Flexible, angled about 45° from the stem. Length: First peduncle: About 6.1 cm. Fourth peduncle: About 8.6 cm. Diameter: About 3 mm. Texture: Pubescent. Color: 146A overlain with anthocyanin, close to 187A.

*Reproductive organs.*—Androecium: Present on disc florets only. Anther color: 12A. Pollen: Scarce. Pollen color: 12A. Gynoecium: Present on both ray and disc florets.

*Seed.*—Seed production has not been observed.

Disease resistance: Plants of the new Chrysanthemum have not been shown to be resistant to pathogens common to Chrysanthemums.

Garden performance: Plants of the new Chrysanthemum have been observed to be tolerant to rain and wind.

It is claimed:

1. A new and distinct cultivar of Chrysanthemum plant named 'Yoandrea', as illustrated and described.

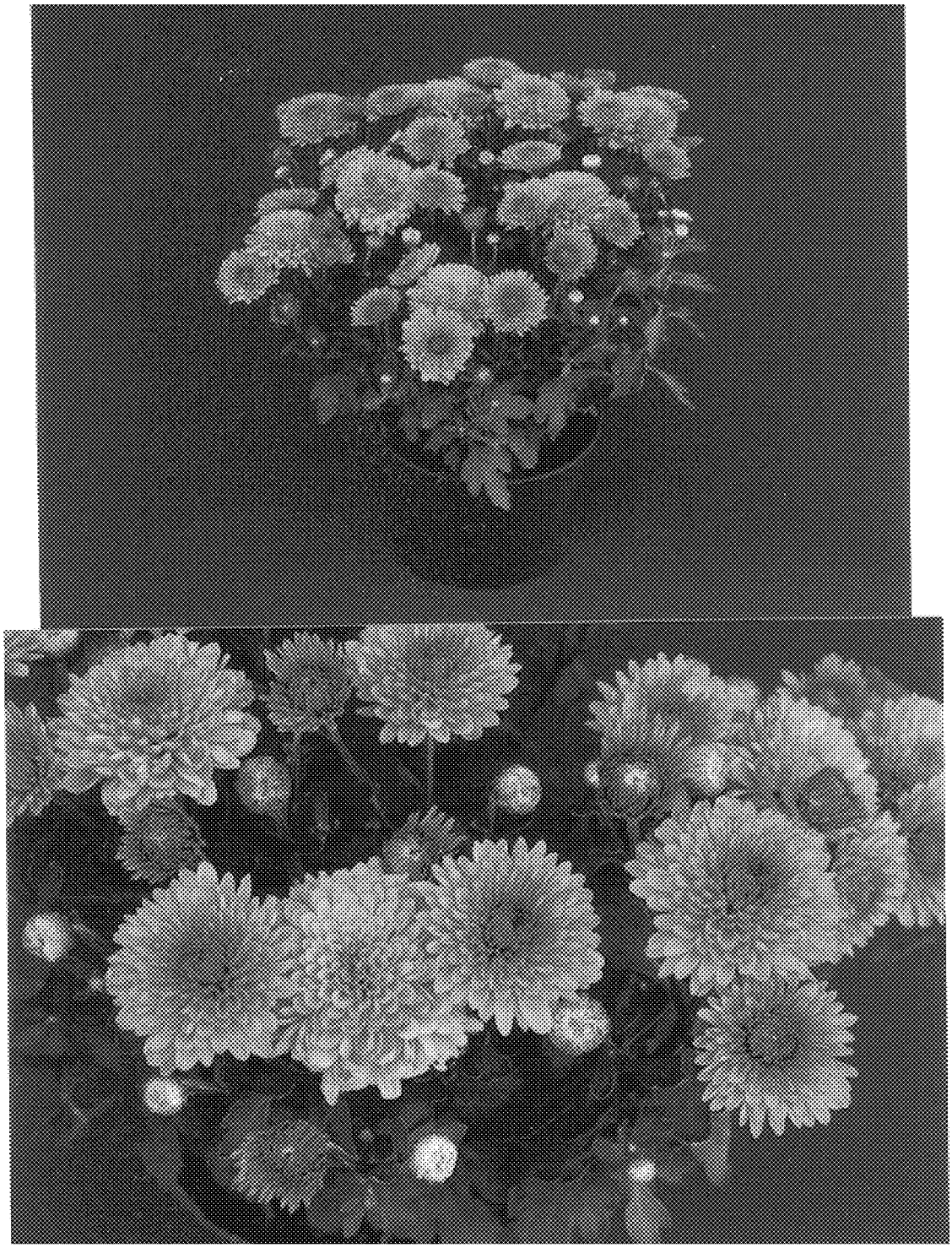

* * * * *